(12) United States Patent
McCoy et al.

(10) Patent No.: US 7,402,237 B2
(45) Date of Patent: Jul. 22, 2008

(54) STEAM CRACKING OF HYDROCARBON FEEDSTOCKS CONTAINING SALT AND/OR PARTICULATE MATTER

(75) Inventors: James N. McCoy, Houston, TX (US); Arthur R. Di Nicolantonio, Seabrook, TX (US); James M. Frye, Houston, TX (US); Melissa D. Stapleton, Beaumont, TX (US); Richard C. Stell, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 685 days.

(21) Appl. No.: 10/975,703

(22) Filed: Oct. 28, 2004

(65) Prior Publication Data

US 2006/0094918 A1    May 4, 2006

(51) Int. Cl.
*C10G 9/00*    (2006.01)
(52) U.S. Cl. .................. 208/128; 208/130; 208/132; 585/648
(58) Field of Classification Search ............. 208/128, 208/130, 132
See application file for complete search history.

(56) References Cited

U.S. PATENT DOCUMENTS

| | | | |
|---|---|---|---|
| 1,936,699 A | 11/1933 | Weaver | |
| 1,984,569 A | 12/1934 | Cooke et al. | 196/66 |
| 2,091,261 A | 8/1937 | Alther | 196/49 |
| 2,158,425 A | 5/1939 | Ragatz | 196/73 |
| 3,291,573 A | 12/1966 | Frescoln | |
| 3,341,429 A | 9/1967 | Fondrk | |
| 3,413,211 A | 11/1968 | Becraft et al. | 208/93 |
| 3,487,006 A | 12/1969 | Newman et al. | 208/93 |
| 3,492,795 A | 2/1970 | Guerrieri | |
| 3,505,210 A | 4/1970 | Wallace et al. | |
| 3,617,493 A | 11/1971 | Wirth et al. | 208/80 |
| 3,677,234 A | 7/1972 | Dutkiewicz | |
| 3,718,709 A | 2/1973 | Simonetta | 260/683 R |
| 3,900,300 A | 8/1975 | Lehman | |
| 4,199,409 A | 4/1980 | Skraba | |
| 4,264,432 A | 4/1981 | Gartside | 208/48 R |
| 4,300,998 A | 11/1981 | Gartside | 208/127 |
| 4,311,580 A | 1/1982 | Bartholic | 208/91 |

(Continued)

FOREIGN PATENT DOCUMENTS

DE    10 93 351    11/1960

(Continued)

OTHER PUBLICATIONS

"Specialty Furnace Design: Steam Reformers and Steam Crackers", presented by T.A. Wells of the M.W. Kellogg Company, 1988 AIChE Spring National Meeting.

(Continued)

*Primary Examiner*—Tam M. Nguyen (57) ABSTRACT

A process for cracking a hydrocarbon feedstock containing salt and/or particulate matter, wherein said hydrocarbon feedstock containing salt and/or particulate matter is heated, then separated into a vapor phase and a liquid phase by flashing in a flash/separation vessel, separating and cracking the vapor phase which comprises less than about 98% of the hydrocarbon feedstock containing salt and/or particulate matter, and recovering cracked product. The salt and/or particulate matter are removed in the liquid bottoms stream from the flash/separation vessel.

25 Claims, 1 Drawing Sheet

U.S. PATENT DOCUMENTS

| | | | |
|---|---|---|---|
| 4,361,478 A | 11/1982 | Gengler et al. | |
| 4,400,182 A | 8/1983 | Davies et al. | |
| 4,426,278 A | 1/1984 | Kosters | 208/130 |
| 4,543,177 A | 9/1985 | Murthy et al. | 208/130 |
| 4,615,795 A | 10/1986 | Woebcke et al. | 208/72 |
| 4,714,109 A | 12/1987 | Tsao | |
| 4,732,740 A | 3/1988 | Woebcke et al. | 422/193 |
| 4,840,725 A | 6/1989 | Paspek | 208/130 |
| 4,854,944 A | 8/1989 | Strong | 48/214 R |
| 4,954,247 A | 9/1990 | Lipkin et al. | |
| 5,096,567 A | 3/1992 | Paspek, Jr. et al. | 208/106 |
| 5,120,892 A | 6/1992 | Skraba | 585/652 |
| 5,141,906 A | 8/1992 | Takeshima et al. | |
| 5,190,634 A | 3/1993 | Fernandez-Baujin et al. | 208/107 |
| 5,468,367 A | 11/1995 | Dickakian et al. | |
| 5,580,443 A | 12/1996 | Yoshida et al. | 208/130 |
| 5,817,226 A | 10/1998 | Lenglet | |
| 5,910,440 A | 6/1999 | Grossman et al. | |
| 6,093,310 A | 7/2000 | Swan | |
| 6,123,830 A | 9/2000 | Gupta et al. | |
| 6,179,997 B1 | 1/2001 | Vedder, Jr. et al. | 208/113 |
| 6,190,533 B1 | 2/2001 | Bradow et al. | |
| 6,210,561 B1 | 4/2001 | Bradow et al. | |
| 6,303,842 B1 | 10/2001 | Bridges et al. | |
| 6,376,732 B1 | 4/2002 | Ngan et al. | |
| 6,632,351 B1 | 10/2003 | Ngan et al. | 208/132 |
| 6,743,961 B2 | 6/2004 | Powers | |
| 2001/0016673 A1 | 8/2001 | Bridges et al. | |
| 2003/0070963 A1 | 4/2003 | Zimmermann et al. | |
| 2004/0004022 A1 | 1/2004 | Stell et al. | 208/106 |
| 2004/0004027 A1 | 1/2004 | Spicer et al. | 208/130 |
| 2004/0004028 A1 | 1/2004 | Stell et al. | 208/130 |
| 2004/0039240 A1 | 2/2004 | Powers | |
| 2004/0054247 A1 | 3/2004 | Powers | |
| 2005/0010075 A1 | 1/2005 | Powers | |

FOREIGN PATENT DOCUMENTS

| | | |
|---|---|---|
| EP | 0063448 | 10/1982 |
| FR | 1472280 | 3/1967 |
| GB | 199 766 | 6/1923 |
| GB | 998 504 | 7/1965 |
| GB | 1 053 751 | 1/1967 |
| GB | 1 203 017 | 8/1970 |
| GB | 1 233 795 | 5/1971 |
| GB | 2 006 259 | 10/1977 |
| GB | 2 012 176 | 11/1977 |
| NL | 7410163 | 4/1975 |
| SU | 1491552 | 7/1989 |
| WO | WO 01/55280 | 8/2001 |
| WO | WO 2004/005433 | 1/2004 |
| ZA | 907394 | 7/1991 |

OTHER PUBLICATIONS

Dennis A. Duncan and Vance A. Ham, Stone & Webster, "The Practicalities of Steam-Cracking Heavy Oil", Mar. 29-Apr. 2, 1992, AIChE Spring National Meeting in New Orleans, LA, pp. 1-41.

ABB Lummus Crest Inc., (presentation) HOPS, "Heavy Oil Processing System", Jun. 15, 1992 TCC PEW Meeting, pp. 1-18.

Mitsui Sekka Engineering Co., Ltd./Mitsui Engineering & Shipbuilding Co., Ltd., "Mitsui Advanced Cracker & Mitsui Innovative Quencher", pp. 1-16.

STEAM CRACKING OF HYDROCARBON FEEDSTOCKS CONTAINING SALT AND/OR PARTICULATE MATTER

FIELD

The present invention relates to the steam cracking of hydrocarbon feedstocks that contain salt and/or particulate matter.

BACKGROUND

Steam cracking, also referred to as pyrolysis, has long been used to crack various hydrocarbon feedstocks into olefins, preferably light olefins such as ethylene, propylene, and butenes. Conventional steam cracking utilizes a pyrolysis furnace which has two main sections: a convection section and a radiant section. The hydrocarbon feedstock typically enters the convection section of the furnace as a liquid (except for light low molecular weight feedstocks which enter as a vapor) wherein it is typically heated and vaporized by indirect contact with hot flue gas from the radiant section and, to a lesser extent, by direct contact with steam. The vaporized feedstock and steam mixture is then introduced into the radiant section where the cracking takes place. Pyrolysis involves heating the feedstock sufficiently to cause thermal decomposition of the larger molecules. The resulting products including olefins leave the pyrolysis furnace for further downstream processing, including quenching.

Crude oil, as produced from the reservoir, is typically accompanied by some volume of saltwater and particulate matter, also known as sediment or mud, from the reservoir formation. As used herein, the term "particulate matter" includes mud, mud blends, mud particles, sediment and other particles included in the hydrocarbon feedstock. Field separation is used to remove the bulk of the saltwater and particulate matter, but some small quantity typically remains in the crude and is reported as basic sediment and water (BS&W) in reporting crude oil quality. Undesalted crude is sometimes processed in a refinery atmospheric pipestill in which the salt and particulate matter will concentrate in the bottoms fraction (atmospheric residue) from distillation of the crude. Additionally, crude or undesalted atmospheric residue can be further contaminated with salt prior to processing by contact with sea water during shipping. Prior to refining, the crude oil, or a bottoms fraction from distillation of the crude oil, is generally passed through a desalter which uses heat, clean water, and an electric current to break the emulsion, thereby releasing water and particulate matter from suspension in the crude oil or bottoms fraction. The salt and some of the particulate matter leave with the desalter effluent water. Some of the particulate matter remains on the bottom of the desalter vessel and is periodically cleaned out. The desalted crude or residue fraction derived from crude leaving the desalter is very low in salt and particulate matter.

In a situation where crude oil, atmospheric residue, or any other hydrocarbon feedstock containing salt and/or particulate matter is used as the feedstock for a reactor, a desalter would constitute a significant additional facility investment. Using undesalted crude oil or undesalted atmospheric residue as a feedstock in a conventional cracking furnace would, however, result in deposition of salt (primarily NaCl) and particulate matter as the liquid hydrocarbon feedstock was vaporized for cracking. Any non-volatile hydrocarbons would cause rapid coking around the dry point. The salt and particulate matter which also lay down cause corrosion of the convection tubes; and if any salt remained in the feed after the dry point and deposited in the radiant section of the furnace, it would result in removal of the protective oxide layer on the radiant tubes. Therefore, provisions must be taken to remove the salt and particulate matter.

Conventional steam cracking systems have been effective for cracking high-quality feedstock which contain a large fraction of volatile hydrocarbons, such as gas oil and naphtha. However, steam cracking economics sometimes favor cracking lower cost heavy feedstocks such as, by way of non-limiting examples, crude oil and atmospheric residue. Crude oil and atmospheric residue often contain high molecular weight, non-volatile components with boiling points in excess of 590° C. (1100° F.) otherwise known as asphaltenes, bitumen, or resid. The non-volatile components of these feedstocks lay down as coke in the convection section of conventional pyrolysis furnaces. Only very low levels of non-volatile components can be tolerated in the convection section downstream of the dry point where the lighter components have fully vaporized.

To address coking problems, U.S. Pat. No. 3,617,493, which is incorporated herein by reference, discloses the use of an external vaporization drum for the crude oil feed and discloses the use of a first flash to remove naphtha as vapor and a second flash to remove vapors with a boiling point between 450 and 1100° F. (230 and 590° C.). The vapors are cracked in the pyrolysis furnace into olefins and the separated liquids from the two flash tanks are removed, stripped with steam, and used as fuel.

U.S. Pat. No. 3,718,709, which is incorporated herein by reference, discloses a process to minimize coke deposition. It describes preheating of heavy feedstock inside or outside a pyrolysis furnace to vaporize about 50% of the heavy feedstock with superheated steam and the removal of the residual, separated liquid. The vaporized hydrocarbons, which contain mostly light volatile hydrocarbons, are subjected to cracking.

U.S. Pat. No. 5,190,634, which is incorporated herein by reference, discloses a process for inhibiting coke formation in a furnace by preheating the feedstock in the presence of a small, critical amount of hydrogen in the convection section. The presence of hydrogen in the convection section inhibits the polymerization reaction of the hydrocarbons thereby inhibiting coke formation.

U.S. Pat. No. 5,580,443, which is incorporated herein by reference, discloses a process wherein the feedstock is first preheated and then withdrawn from a preheater in the convection section of the pyrolysis furnace. This preheated feedstock is then mixed with a predetermined amount of steam (the dilution steam) and is then introduced into a gas-liquid separator to separate and remove a required proportion of the non-volatiles as liquid from the separator. The separated vapor from the gas-liquid separator is returned to the pyrolysis furnace for heating and cracking.

U.S. patent application Ser. No. 10/188,461, filed Jul. 3, 2002, which is fully incorporated herein by reference, describes a process for cracking heavy hydrocarbon feedstock which mixes heavy hydrocarbon feedstock with a fluid, e.g., hydrocarbon or water, to form a mixture stream which is flashed to form a vapor phase and a liquid phase, the vapor phase being subsequently cracked to provide olefins. The amount of fluid mixed with the feedstock is varied in accordance with a selected operating parameter of the process, e.g., temperature of the mixture stream before the mixture stream is flashed, the pressure of the flash, the flow rate of the mixture stream, and/or the excess oxygen in the flue gas of the furnace.

While the references address the use of heavier hydrocarbon feedstocks, none of the references address the possibility of using an undesalted hydrocarbon feedstock for a cracking furnace. It has now surprisingly been found that it is possible to operate a steam cracking furnace with a hydrocarbon feedstock containing salt and/or particulate matter. This is particularly advantageous when the feedstock additionally contains non-volatile components.

SUMMARY

The present invention relates to a process for cracking a hydrocarbon feedstock containing salt and/or particulate matter. The process comprises: (a) heating the hydrocarbon feedstock containing salt and/or particulate matter; (b) feeding the hydrocarbon feedstock containing salt and/or particulate matter to a flash/separation vessel; (c) separating the hydrocarbon feedstock containing salt and/or particulate matter into a vapor phase and a liquid phase, such that the liquid phase comprises a sufficient portion of the hydrocarbon feedstock to maintain salt and/or particulate matter in suspension; (d) removing the vapor phase from the flash/separation vessel; and (e) cracking the vapor phase to produce an effluent comprising olefins. Steam, which may optionally comprise sour or treated process steam and may optionally be superheated, may be added at any step or steps in the process prior to cracking the vapor phase.

In one embodiment where the hydrocarbon feedstock containing salt also contains non-volatile components, the process comprises: (a) heating the hydrocarbon feedstock containing salt to a first temperature; (b) adding steam to the hydrocarbon feedstock containing salt; (c) further heating the hydrocarbon feedstock containing salt to a second temperature greater than the first temperature, where the second temperature is such that a sufficient portion of the hydrocarbon feedstock containing salt remains in the liquid phase to maintain salt in suspension; (d) feeding the hydrocarbon feedstock containing salt to a flash/separation vessel; (e) separating the hydrocarbon feedstock containing salt into a vapor phase and a liquid phase, where the liquid phase is rich in non-volatile components and salt and the vapor phase is substantially depleted of non-volatile components and salt; (f) removing the vapor phase from the flash/separation vessel; (g) optionally adding steam to the vapor phase; and (h) cracking the vapor phase in a radiant section of a pyrolysis furnace to produce an effluent comprising olefins, the pyrolysis furnace comprising a radiant section and a convection section.

Preferably the liquid phase in the flash/separation vessel comprises at least about 2%, for example about 5%, of the hydrocarbon feedstock containing salt and/or particulate matter. If necessary to maintain this condition, e.g. when the hydrocarbon feedstock is relatively light, such as a light crude mixed with condensate, heavy hydrocarbon feedstock may be added to the hydrocarbon feedstock containing salt and/or particulate matter. The addition of heavy hydrocarbon feedstock reduces the deposition of salt and/or particulate matter in and upstream of the flash/separation vessel and ensures that the liquid stream leaving the flash/separation vessel comprises a sufficient percentage of the total hydrocarbon feedstock to avoid deposition of salt and/or particulate matter upstream of the flash separation vessel.

DETAILED DESCRIPTION

Unless otherwise stated, all percentages, parts, ratios, etc. are by weight. Unless otherwise stated, a reference to a compound or component includes the compound or component by itself, as well as in combination with other compounds or components, such as mixtures of compounds.

Further, when an amount, concentration, or other value or parameter is given as a list of upper preferable values and lower preferable values, this is to be understood as specifically disclosing all ranges formed from any pair of an upper preferred value and a lower preferred value, regardless of whether ranges are separately disclosed.

As used herein, non-volatile components are the fraction of a hydrocarbon stream with a nominal boiling point above 590° C. (1100° F.) as measured by ASTM D-6352-98 or D-2887. This invention works very well with non-volatile components having a nominal boiling point above 760° C. (1400° F.). The boiling point distribution of the hydrocarbon stream is measured by Gas Chromatograph Distillation (GCD) according to the methods described in ASTM D-6352-98 or D-2887, extended by extrapolation for materials boiling above 700° C. (1292° F.). Non-volatile components can include coke precursors, which are moderately heavy and/or reactive molecules, such as multi-ring aromatic compounds, which can condense from the vapor phase and then form coke under the operating conditions encountered in the present process of the invention. $T_{50}$ as used herein shall mean the temperature, determined according to the boiling point distribution described above, at which 50 weight percent of a particular hydrocarbon sample has reached its boiling point. Likewise $T_{95}$ or $T_{98}$ mean the temperature at which 95 or 98 weight percent, respectively, of a particular sample has reached its boiling point. Nominal final boiling point shall mean the temperature at which 99.5 weight percent of a particular sample has reached its boiling point.

The hydrocarbon feedstock for use in the present invention typically comprises one or more of gas oils, heating oil, diesel, hydrocrackate, Fischer-Tropsch liquids, distillate, heavy gas oil, steam cracked gas oil and residues, crude oil, atmospheric pipestill bottoms, vacuum pipestill streams including bottoms, heavy non-virgin hydrocarbon streams from refineries, vacuum gas oils, low sulfur waxy residue, heavy waxes, atmospheric residue, and heavy residue and further comprises salt and/or particulate matter.

For ease of reference herein, the term "undesalted" will be understood to mean that a feedstock contains salt(s) and/or particulate matter that would conventionally be removed in a desalter, whether the salt and/or particulate matter was present in the produced crude oil stream or was a contaminant added to a hydrocarbon feedstock during shipping and handling. In a preferred embodiment, the hydrocarbon feedstock comprising salt and/or particulate matter, or undesalted hydrocarbon feedstock, further comprises non-volatile components. The salt typically comprises primarily sodium chloride, with lesser amounts of potassium chloride and/or magnesium chloride.

Aside from physical blockage due to deposition in the exchanger tubes, sodium can cause corrosion of the convection tubes and removal of the radiant tube protective oxide layer. For this reason, sodium (and salt) concentrations in the feed to a pyrolysis furnace must be controlled carefully.

Because of the extremely low acceptable concentration of sodium in the radiant section of steam cracking furnaces, it is usual to purchase a desalter for removing the salt and particulate matter from crude or crude residues prior to steam cracking. While acceptable salt and/or particulate matter concentrations will vary with furnace design, desalters are generally considered necessary when sodium chloride is greater than a few ppm by weight of the feedstock, depending on the operating conditions for a given feedstock. However, if a flash/separation vessel is used upstream of the dry point for the hydrocarbon stream, it is possible to operate in such a way that undesalted crude and crude residues can be used as a feedstock to a hydrocarbon cracking unit. Indications are that sodium in the vapor phase can be controlled within acceptable limits, and that virtually all of the salt and particulate matter will remain in the liquid phase in a flash/separation vessel as long as less than about 98% of the hydrocarbon is a vapor at the inlet of the flash/separation vessel. For the purposes of this invention, "a sufficient portion of the hydrocarbon feedstock to maintain salt and/or particulate matter in suspension" shall mean the lesser of (a) 2% of the hydrocarbon content of the stream entering the flash/separation vessel or (b) the percentage of the hydrocarbon content sufficient to suspend enough salt and/or particulate matter to prevent deposition on the convection tubes.

The objective of this invention is to maintain sufficient liquid velocity at all points in the convection section upstream of the flash/separation vessel such that the salt and/or particulate matter contained in the undesalted hydrocarbon feedstock remain in suspension until they are removed in the liquid phase leaving the flash/separation vessel. Upstream of the addition of steam or other fluids, the undesalted hydrocarbon feedstock will be primarily in the liquid phase and will generally have sufficient turbulence to maintain the salt and/or particulate matter in suspension. Once the hydrocarbon feedstock containing salt and/or particulate matter is mixed with dilution steam, the total flow stream will have enough velocity, kinetic energy, and turbulence to keep the particulate matter and salt moving through the convection section upstream of the flash/separation vessel as long as a sufficient portion of the stream is liquid. The liquid fraction required will vary with the properties of the hydrocarbons remaining in the liquid phase, the velocity of the flow stream, and the quantity of salt and/or particulate matter in the flow stream. Lower liquid fractions are required for more viscous, generally heavier, liquid phase hydrocarbons. A higher liquid fraction would be required if the flow stream velocity were relatively low. Generally, maintaining about 2% of the total hydrocarbon, on a weight basis, in the liquid phase would be sufficient to maintain salt and/or particulate matter in suspension. A 5% liquid cut would often be preferred.

If no deposits form in the tubes upstream of the flash/separation vessel, then the salt and/or particulate matter can be removed with the bottoms liquid stream from the flash/separation vessel. The liquid phase could then be sold as bunker C fuel oil or fed to a refinery catalytic cracker or coker unit without desalting. If a cleaner bottoms liquid stream is required, for example as feed to a boiler, a small desalter can be used to remove the salt and particulate matter in the flash/separation vessel bottoms liquid stream at a cost far less than would be required for desalting the total feed to the furnace. This process would allow cracking crude oils, residues derived from crudes, and other hydrocarbon feedstocks containing salt and/or particulate matter by using a flash/separation vessel without the investment required for up-front desalting.

Should liquid velocities through the upper convection section before the flash/separation vessel ever be so low that salt and/or particulate matter did deposit in these tubes thus reducing heat transfer, it would be possible in most systems to flush the tubes with water during typical operations, including decoking operations.

Sodium salts can cause corrosion of convection section tubes if they deposit on a tube surface and are not removed for long periods of time. The effect is accelerated if the sodium is ionized in liquid water present in the hydrocarbon feed. Further, if sodium were not removed upstream of the radiant section, some of the sodium would deposit in radiant section coke. Sodium would catalyze increased coking in the radiant section, and could also catalyze a side reaction between dilution steam and the hydrocarbon feedstock to produce increased levels of CO and $CO_2$. High CO levels can cause a plant shutdown by increasing some downstream process temperatures, and $CO_2$ is recovered in the ethylene product, potentially causing difficulties with meeting product specifications if product treatment is not sufficient to remove it. The damage that sodium causes to the radiant metallurgy typically occurs during offline decoking with air. At normal decoking temperatures, sodium chloride present in the coke would melt and the molten sodium chloride would react with the chromium in the protective chromium oxide layer in the radiant section to form volatile sodium chromate. This would result in an oxide layer containing nickel and iron oxide in addition to $Cr_2O_3$. The radiant metallurgy is typically an alloy of Cr, Fe, Ni, and small amounts of other elements. During pretreatment the chromium in the alloy migrates to the inside surface of the tube where it becomes a $Cr_2O_3$ layer. When Na removes this layer, the Fe and Ni behind it oxidize. The nickel oxide and iron oxide would catalyze increased radiant section coking on subsequent runs and, during decoking operation, would catalyze decoking that results in coke spalls that can plug radiant section tubes. Because of the damaging effects of sodium, it is advantageous to use the flash/separation vessel to remove almost all salts from an undesalted hydrocarbon feedstock. The flash/separation vessel can be operated so as to remove sodium to required levels for the furnace.

Vanadium, which is occasionally present in hydrocarbon feedstocks, may form vanadium pentoxide during normal cracking since steam is present, and vanadium that deposits in coke would form vanadium pentoxide during steam air decoking. Vanadium pentoxide would destroy the protective chromium oxide layer in the radiant tubes, thereby causing fast carburization of the tubes and rapid coking in subsequent operations. Vanadium pentoxide would also destroy the protective oxide layer on 304 stainless steel tubes as would generally be used in the lower part of the convection section. Preferably, vanadium in the feedstock is limited to less than 1 ppm, especially downstream of the flash/separation vessel. Vanadium levels vary significantly among crudes and many have low enough levels to be of no concern. Most crude oils have vanadium components only in the portions of the crude boiling at temperatures above about 950° F., which generally leave the process as part of the liquid phase leaving the flash/separation vessel. A relatively low percentage of crude oils have vanadium in the 650 to 950° F. boiling range fraction, and these crudes can be avoided if vanadium levels downstream of the separator drum are too high.

Much of the salt in undesalted crude or crude residue comprises sodium chloride. The chloride portion of the salt is not problematic when the salt is in the solid phase or when the chloride, as HCl, is in the vapor phase. However, if water is mixed with the undesalted feed at the top of the convection section, the sodium and chloride will dissociate. The chloride ions formed upon mixing with water can cause stress corrosion cracking of stainless steel in the convection rows where water is present, until the water completely vaporizes. Although injected water can be used to control temperature, thereby controlling the vapor liquid split in the flash/separation vessel, it is preferred for this invention that the vapor liquid split in the flash/separation vessel be controlled by using variable levels of steam as a diluent, by varying furnace excess air, and/or by mixing in a heavier hydrocarbon feedstock if necessary to maintain the desired vapor liquid split in the flash/separation vessel.

Potassium chloride is also present in some crude oils and its effects are similar to those of sodium chloride. Magnesium chloride also generally carries the same risks as sodium chloride, but magnesium is less harmful to the furnace than sodium. All of these salts can be removed using the process of this invention.

In order to prevent deposition of salt and/or particulate matter in the convection section tube banks and the flash/separation vessel, it is preferable to operate the flash/separation vessel at conditions such that at least about 2% of the hydrocarbon stream remains in the liquid phase at all points upstream of the flash/separation vessel. In some cases an undesalted hydrocarbon feedstock may not have a sufficient quantity of high molecular weight or low volatility hydrocarbon components to maintain the 2% liquid phase at the desired operating temperatures. In that event, an optional heavy hydrocarbon feedstock may be added to form a hydrocarbon feedstock containing salt and/or particulate matter with properties sufficient to maintain the desired liquid fraction at the desired operating conditions.

The optional heavy hydrocarbon feedstock for use with the present invention would preferably contain one or more of atmospheric residue, vacuum residue, a heavier crude oil, heavy non-virgin hydrocarbon streams from refineries, and low sulfur waxy residue. One preferred heavy hydrocarbon feedstock is an economically advantaged, minimally processed heavy hydrocarbon stream containing non-volatile hydrocarbons and/or coke precursors. Another preferred heavy hydrocarbon feedstock for use in this invention is an atmospheric residue, also known as an atmospheric pipestill bottoms stream.

The optional heavy hydrocarbon feedstock will preferably have a higher $T_{50}$ boiling point than the hydrocarbon feedstock containing salt and/or particulate matter, but may have a nominal final boiling point below, equal to, or greater than the nominal final boiling point of the hydrocarbon feedstock containing salt and/or particulate matter. Likewise the initial boiling point of the heavy hydrocarbon feedstock may be lower than, equal to, or greater than the initial boiling point of the hydrocarbon feedstock containing salt and/or particulate matter, but will generally be at least about 56° C. (about 100° F.) higher, more typically at least about 280° C. (about 500° F.), and often more than about 390° C. (about 700° F.) higher.

Preferably, the addition of the heavy hydrocarbon feedstock will result in a hydrocarbon feedstock blend containing salt and/or particulate matter with a $T_{98}$ boiling point at least about 28° C. (about 50° F.) higher than the $T_{98}$ boiling point of the original hydrocarbon feedstock, for example at least about 56° C. (about 100° F.) higher, as a further example at least about 111° C. (about 200° F.) higher, and as yet another example at least about 167° C. (about 300° F.) higher. Preferably, the addition of the heavy hydrocarbon feedstock will also result in a hydrocarbon feedstock blend containing salt and/or particulate matter with a $T_{95}$ boiling point at least about 14° C. (about 25° F.) higher than the $T_{95}$ boiling point of the original hydrocarbon feedstock, such as at least about 28° C. (about 50° F.) higher, for example at least about 56° C. (about 100° F.) higher, as a further example at least about 111° C. (about 200° F.) higher, and as yet another example at least about 167° C. (about 300° F.) higher.

Vapor-liquid equilibrium modeling using computer software, such as PROVISION™ by Simulation Sciences Inc., can be used to determine optimal quantities of a given heavy hydrocarbon feedstock for use with a given hydrocarbon feedstock containing salt and/or particulate matter. Considerations in this determination would be optimization of total fluid velocity to minimize any settling of salt and/or particulate matter particles, preferably with maintenance of at least about 2% of the hydrocarbon feedstock blend in the liquid phase.

The present invention relates to a process for heating and steam cracking a hydrocarbon feedstock containing salt and/or particulate matter. The process comprises heating a hydrocarbon feedstock containing salt and/or particulate matter, flashing the hydrocarbon feedstock containing salt and/or particulate matter to form a vapor phase and a liquid phase, such that the liquid phase comprises a sufficient portion of the hydrocarbon feedstock to maintain salt and/or particulate matter in suspension, feeding the vapor phase to the radiant section of a pyrolysis furnace, and producing an effluent comprising olefins.

The addition of steam at various points is disclosed elsewhere and will, for simplicity, not be detailed in every description herein. It is further noted that any of the steam added may comprise sour steam or treated process steam and that any of the steam added, whether sour or not, may be superheated. Superheating is preferable when the steam comprises sour steam. Since steam and other fluids may be added at various points, the description herein will use the term "hydrocarbon feedstock containing salt and/or particulate matter" to mean the components of the hydrocarbon feedstock and the optional heavy hydrocarbon feedstock together as they travel through the process regardless of what quantities of steam and other fluids may also be present at any given stage.

When light hydrocarbon feedstock having essentially no non-volatile components and/or coke precursors is cracked, the feed is typically preheated in the upper convection section of a pyrolysis furnace, optionally mixed with steam, and then further preheated in the convection section, where essentially all of the light hydrocarbon feedstock vaporizes forming a vapor phase which is the fed to the radiant section of the furnace for pyrolysis. Contamination of the light hydrocarbon feedstock with non-volatile components and/or coke precursors would, however, result in extensive coke formation in the convection tubes in that process. This concern was partially addressed in U.S. Pat. No. 5,580,443, which discloses a process wherein the feedstock is first preheated, then withdrawn from a preheater in the convection section of the pyrolysis furnace, mixed with a predetermined amount of steam, introduced into a gas-liquid separator to separate and remove a required proportion of the non-volatiles as liquid from the separator. The separated vapor from the gas-liquid separator is returned to the pyrolysis furnace for heating and cracking.

In the process of the present invention, it is desirable to maintain a liquid phase with sufficient velocity to minimize deposition of salt and/or particulate matter on the walls of the convection section tubes. Because water will ionize most salts present in a hydrocarbon feedstock, thereby accelerating corrosion of stainless steel convection tubes upstream of the flash/separation vessel, it is preferable in the implementation of this invention that the injection of water be avoided or minimized, particularly when austenitic stainless steel tubes are present. If water injection is necessary then 5Cr or 9 Cr (i.e., 5% or 9% chromium in a steel alloy) tubes are preferred as they are not susceptible to chloride stress corrosion cracking.

It will be recognized that economic considerations would generally favor maximizing the fraction of the feedstock which is in the vapor phase and subsequently cracked. In this case, however, maximizing the vapor phase is not practical to the same extent as it might be for other feedstocks. In order to maintain sufficient liquid to both ensure that all surfaces are wetted adequately to prevent coke formation and that there is sufficient liquid velocity to minimize deposition of salt and/or particulate matter, it is preferable to operate the flash/separation vessel at conditions which result in at least about 2% of the total hydrocarbon remaining in the liquid phase.

Addition of a heavy hydrocarbon feedstock to the hydrocarbon feedstock containing salt and/or particulate matter can increase the percentage of the hydrocarbon feedstock vaporized while reducing the risk of salt and/or particulate matter deposition on the tube walls. In addition, depending on the heavy hydrocarbon feedstock used, a fraction of the heavy hydrocarbon feedstock will be vaporized and subsequently available for cracking.

The heavy hydrocarbon feedstock, when mixed with the hydrocarbon feedstock containing salt and/or particulate matter may be from about 2 to about 75 percent of the mixture of the hydrocarbon feedstock containing salt and/or particulate matter and the heavy hydrocarbon feedstock, for example from about 2% to about 60%, and as a further example from about 10% to about 50%. The percentage of the heavy hydrocarbon feedstock added to the hydrocarbon feedstock containing salt and/or particulate matter can be optimized according to economics and availability of given hydrocarbon streams at any particular time. However, for the purposes of the present invention, it is preferable that the quantity of heavy hydrocarbon feedstock added is sufficient to result in a liquid fraction of at least about 2% of the total hydrocarbon flow into the flash/separation vessel, and generally in the range of about 5 up to about 50%, more preferably about 5 up to about 30%. It is noted that the lighter the heavy hydrocarbon feedstock is relative to the hydrocarbon feedstock containing salt and/or particulate matter being used, the more heavy hydrocarbon feedstock will be required for optimal benefit.

Depending on tankage available, the optional heavy hydrocarbon feedstock may be added to the hydrocarbon feedstock containing salt and/or particulate matter in the feedstock storage tanks or at any point prior to introduction of the hydrocarbon feedstock containing salt and/or particulate matter to the convection section of the furnace. In order to maximize the fluid velocity and minimize deposition of salt and/or particulate matter, it is preferable to add the heavy hydrocarbon feedstock prior to any heating of the hydrocarbon feedstock containing salt and/or particulate matter. Preferably, both the heavy hydrocarbon feedstock and the hydrocarbon feedstock containing salt and/or particulate matter are at a sufficient temperature to ensure flowability of both the heavy hydrocarbon feedstock and the blended feedstock upon mixing.

Figure 1:
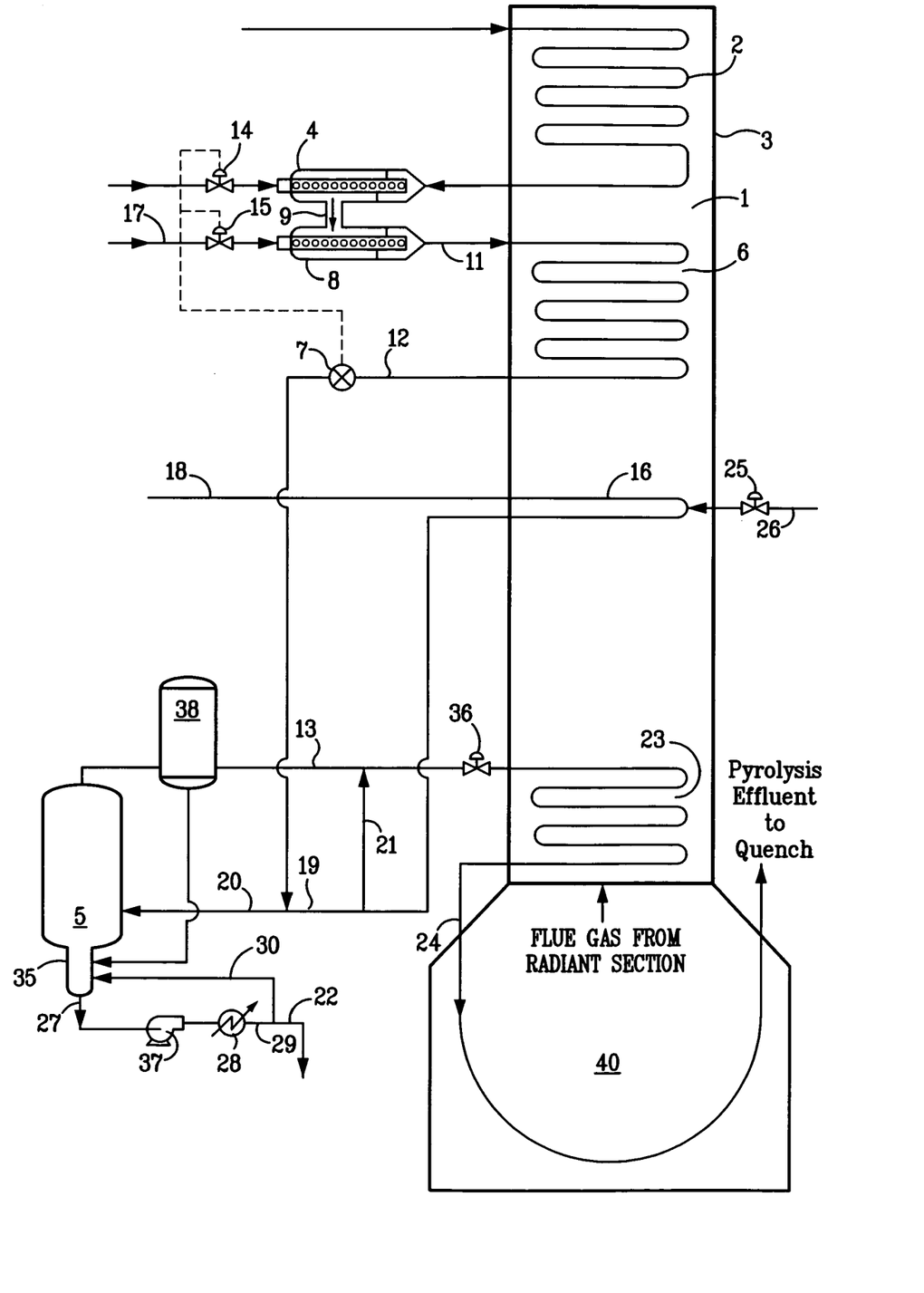
FIG. 1 illustrates a schematic flow diagram of the overall process and apparatus in accordance with the present invention employed with a pyrolysis furnace.

After blending the heavy hydrocarbon feedstock with a hydrocarbon feedstock containing salt and/or particulate matter to produce a hydrocarbon feedstock blend containing salt and/or particulate matter, the heating of the hydrocarbon feedstock blend containing salt and/or particulate matter can take any form known by those of ordinary skill in the art. Referring now to FIG. 1, in a preferred embodiment, the heating comprises indirect contact of the hydrocarbon feedstock blend containing salt and/or particulate matter in the upper (farthest from the radiant section 40) convection section tube bank 2 of the furnace 1 with hot flue gases from the radiant section 40 of the furnace 1. For ease of reference herein, all references to hydrocarbon feedstock containing salt and/or particulate matter, such as particulate matter, subsequent to entry in the first convection section tube bank will be deemed to include any optional heavy hydrocarbon feedstock that has been added to the stream.

Heating in the convection section can be accomplished, by way of non-limiting example, by passing the hydrocarbon feedstock containing salt and/or particulate matter through a bank of heat exchange tubes 2 located within the convection section 3 of the furnace 1. The heated hydrocarbon feedstock containing salt and/or particulate matter typically has a temperature between about 150 and about 340° C. (about 300 and about 650° F.), such as about 160 to about 230° C. (about 325 to about 450° F.), for example about 170 to about 220° C. (about 340 to about 425° F.). In any event, the temperature is preferably controlled to ensure that at least about 2% of the hydrocarbon feedstock containing salt and/or particulate matter remains in the liquid phase.

The heated hydrocarbon feedstock containing salt and/or particulate matter may be mixed with primary dilution steam and, optionally, a fluid which can be a hydrocarbon, preferably liquid but optionally vapor; water; steam; or a mixture thereof. The temperature of the fluid can be below, equal to, or above the temperature of the heated feedstock. In one possible embodiment, the fluid latent heat of vaporization can be used to control the hydrocarbon feedstock containing salt and/or particulate matter temperature entering the flash/separation vessel.

The mixing of the heated hydrocarbon feedstock containing salt and/or particulate matter, primary dilution steam, and the optional fluid can occur inside or outside the pyrolysis furnace 1, but preferably it occurs outside the furnace 1. The mixing can be accomplished using any mixing device known within the art. For example, it is possible to use a first sparger 4 of a double sparger assembly 9 for the mixing. The first sparger 4 can avoid or reduce hammering, caused by sudden vaporization of the fluid, upon introduction of the fluid into the heated hydrocarbon feedstock.

The use of steam and or fluid mixed with the hydrocarbon feedstock containing salt and/or particulate matter is optional for high volatility feedstocks. It is possible that such feedstocks can be heated in any manner known in the industry, for example in heat exchange tubes 2 located within the convection section 3 of the furnace 1. The hydrocarbon feedstock containing salt and/or particulate matter could be conveyed to the flash/separation vessel with little or no added steam or fluid.

The primary dilution steam 17 can have a temperature greater, lower or about the same as hydrocarbon feedstock containing salt and/or particulate matter mixture but preferably the temperature is about the same as that of the mixture, which is preferably about 350° F. The primary dilution steam 17 may be superheated before being injected into the second sparger 8.

The mixture stream comprising the heated hydrocarbon feedstock containing salt and/or particulate matter, the fluid, and the optional primary dilution steam stream leaving the second sparger 8 is optionally heated further in the convection section of the pyrolysis furnace 3 before the flash. The heating can be accomplished, by way of non-limiting example, by passing the mixture stream through a bank of heat exchange tubes 6 located within the convection section, usually as a lower part of the first convection section tube bank, of the furnace and thus heated by the hot flue gas from the radiant section of the furnace. The thus-heated hydrocarbon feedstock containing salt and/or particulate matter leaves the convection section as part of a mixture stream 12 to optionally be further mixed with an additional steam stream 18.

Optionally, the secondary dilution steam stream 18 can be further split into a flash steam stream 19 which is mixed with the hydrocarbon mixture 12 before the flash and a bypass steam stream 21 which bypasses the flash of the hydrocarbon mixture and, instead is mixed with the vapor phase from the flash before the vapor phase is further heated in the lower convection section and then cracked in the radiant section of the furnace. The present invention can operate with all secondary dilution steam 18 used as flash steam 19 with no bypass steam 21. Alternatively, the present invention can be operated with secondary dilution steam 18 directed to bypass steam 21 with no flash steam 19. In a preferred embodiment in accordance with the present invention, the ratio of the flash steam stream 19 to bypass steam stream 21 should be preferably 1:20 to 20:1, and most preferably 1:2 to 2:1. In this embodiment, the flash steam 19 is mixed with the hydrocarbon mixture stream 12 to form a flash stream 20 before the flash in flash/separation vessel 5. Preferably, the secondary dilution steam stream is superheated in a superheater section 16 in the furnace convection 2 before splitting and mixing with the hydrocarbon mixture. The addition of the flash steam stream 19 to the hydrocarbon mixture stream 12 aids the vaporization of less volatile components of the mixture before the flash stream 20 enters the flash/separation vessel 5.

A second optional fluid can be added to the mixture stream before flashing the mixture stream, the second fluid being a hydrocarbon vapor.

The mixture stream 12 or the flash stream 20 is then flashed, for example in a flash/separation vessel 5, for separation into two phases: a vapor phase comprising predominantly steam and volatile hydrocarbons from the hydrocarbon feedstock containing salt and/or particulate matter and a liquid phase comprising less-volatile hydrocarbons along with a significant fraction of the non-volatile components and/or coke precursors and a significant fraction of the salt and/or particulate matter. It is understood that vapor-liquid equilibrium at the operating conditions described herein would result in very small quantities of non-volatile components and/or coke precursors present in the vapor phase. Additionally, and varying with the design of the flash/separation vessel, minute quantities of liquid containing non-volatile components and/or salt and/or particulate matter could be entrained in the vapor phase. In the process of this invention, these quantities are sufficiently small to allow decoking downstream of the flash/separation vessel on the same schedule as for decoking in the radiant section of the furnace. The vapor phase can be considered to have substantially no non-volatile components or coke precursors when coke buildup in the convection section between the flash/separation vessel is at a sufficiently low rate that decoking is not required any more frequently than typical decoking required for the radiant section is required.

For ease of description herein, the term flash/separation vessel will be used to mean any vessel or vessels used to separate the hydrocarbon feedstock containing salt and/or particulate matter into a vapor phase and at least one liquid phase. It is intended to include fractionation and any other method of separation, for example, but not limited to, drums, distillation towers, and centrifugal separators.

The mixture stream 12 is preferably introduced tangentially to the flash/separation vessel 5 through at least one side inlet located in the side of said vessel. The vapor phase is preferably removed from the flash/separation vessel as an overhead vapor stream 13. The vapor phase, preferably, is fed back to a convection section tube bank 23 of the furnace, preferably located nearest the radiant section 40 of the furnace 1, for optional heating and is then conveyed through crossover pipes 24 to the radiant section 40 of the pyrolysis furnace for cracking. The liquid phase of the flashed mixture stream is removed from the flash/separation vessel 5, preferably as a bottoms stream 27.

It is preferred to maintain a predetermined constant ratio of vapor to liquid in the flash/separation vessel 5, but such ratio is difficult to measure and control. As an alternative, the temperature of the mixture stream 12 before the flash/separation vessel 5 can be used as an indirect parameter to measure, control, and maintain an approximately constant vapor to liquid ratio in the flash/separation vessel 5. Ideally, when the mixture stream temperature is higher, more volatile hydrocarbons will be vaporized and become available, as part of the vapor phase, for cracking. However, when the mixture stream temperature is too high, more heavy hydrocarbons, including coke precursors, will be present in the vapor phase and carried over to the convection furnace tubes, eventually coking the tubes. If the mixture stream 12 temperature is too low, resulting in a low ratio of vapor to liquid in the flash/separation vessel 5, more volatile hydrocarbons will remain in liquid phase and thus will not be available for cracking.

The mixture stream temperature is controlled to maximize recovery or vaporization of volatiles in the feedstock while avoiding excessive deposition of salt and/or particulate matter or coking in the furnace tubes or in piping and vessels conveying the mixture from the flash/separation vessel 5 to the furnace 1 via line 13. The pressure drop across the piping and vessels 13 conveying the mixture to the lower convection section 23, and the crossover piping 24, and the temperature rise across the lower convection section 23 may be monitored to detect the onset of coking problems. For instance, if the crossover pressure and process inlet pressure to the lower convection section 23 begin to increase rapidly due to coking, the temperature in the flash/separation vessel 5 and the mixture stream 12 should be reduced. If coking occurs in the lower convection section 23, the temperature of the flue gas increases to the sections above, such as the optional superheater 16. If a superheater 16 is present, the increased flue gas temperature can be offset in part by adding more desuperheater water 26.

The selection of the mixture stream 12 temperature is also determined by the composition of the feedstock materials. When the feedstock contains higher amounts of lighter hydrocarbons, the temperature of the mixture stream 12 can be set lower. When the feedstock contains a higher amount of less- or non-volatile hydrocarbons, the temperature of the mixture stream 12 should be set higher.

Typically, the temperature of the mixture stream 12 can be set and controlled at between about 315 and about 540° C. (about 600 and about 1000° F.), such as between about 370 and about 510° C. (about 700 and about 950° F.), for example between about 400 and about 480° C. (about 750 and about 900° F.), and often between about 430 and about 475° C. (about 810 and about 890° F.). These values will change with the volatility of the feedstock as discussed above.

Considerations in determining the temperature include the desire to maintain a liquid phase to reduce or eliminate the likelihood of solids deposition or coke formation in the flash/separation vessel 5 and associated piping and on convection tubes upstream of the flash/separation vessel 5. Typically, at least about 2%, more preferably about 5%, of the total hydrocarbons are in the liquid phase after being flashed.

It is desirable to maintain a constant temperature for the mixture stream 12 mixing with flash steam 19 and entering the flash/separation vessel to achieve a constant ratio of vapor to liquid in the flash/separation vessel 5, and to avoid substantial temperature and flash vapor to liquid ratio variations. One possible control arrangement is the use of a control system 7 to automatically control the fluid valve 14 and primary dilution steam valve 15 on the two spargers to maintain a set temperature for the mixture stream 12 before the flash/separation vessel 5. When the control system 7 detects a drop of temperature of the mixture stream, it will cause the fluid valve 14 to reduce the injection of the fluid into the first sparger 4. If the temperature of the mixture stream starts to rise, the fluid valve will be opened wider to increase the injection of the fluid into the first sparger 4. It is preferred in the process of this invention that injected water be minimized.

When the primary dilution steam stream 17 is injected to the second sparger 8, the temperature control system 7 can also be used to control the primary dilution steam valve 15 to adjust the amount of primary dilution steam stream injected to the second sparger 8. This further reduces the sharp variation of temperature changes in the flash 5. When the control system 7 detects a drop of temperature of the mixture stream 12, it will instruct the primary dilution steam valve 15 to increase the injection of the primary dilution steam stream into the second sparger 8 while valve 14 is closed more. If the temperature starts to rise, the primary dilution steam valve will automatically close more to reduce the primary dilution steam stream injected into the second sparger 8 while valve 14 is opened wider.

In an example embodiment, the amount of fluid and primary dilution steam vary to maintain a constant mixture stream temperature 12, while preferably maintaining a constant ratio of $H_2O$ to feedstock in the mixture 11. However, while water is a preferred fluid for use in this invention, it is generally feasible to operate with no added fluid other than steam. To further avoid sharp variation of the flash temperature, the present invention also preferably utilizes an intermediate desuperheater 25 in the superheating section of the secondary dilution steam in the furnace. This allows the superheater 16 outlet temperature to be controlled at a constant value, independent of furnace load changes, coking extent changes, excess oxygen level changes, and other variables. Normally, this desuperheater 25 maintains the temperature of the secondary dilution steam between about 425 and about 590° C. (about 800 and about 1100° F.), for example between about 455 and about 540° C. (about 850 and about 1000° F.), such as between about 455 and about 510° C. (about 850 and about 950° F.). The desuperheater 25 can be a control valve and water atomizer nozzle. After partial preheating, the secondary dilution steam exits the convection section and a fine mist of desuperheater water 26 can be added which rapidly vaporizes and reduces the temperature. The steam is preferably then further heated in the convection section. The amount of water added to the superheater can control the temperature of the steam which is mixed with mixture stream 12.

In addition to maintaining a constant temperature of the mixture stream 12 entering the flash/separation vessel 5, it is generally also desirable to maintain a constant hydrocarbon partial pressure of the flash stream 20 in order to maintain a constant ratio of vapor to liquid in the flash/separation vessel 5. By way of examples, the constant hydrocarbon partial pressure can be maintained by maintaining constant flash/separation vessel pressure through the use of control valves 36 on the vapor phase line 13, and by controlling the ratio of steam to hydrocarbon feedstock containing salt and/or particulate matter in stream 20.

Typically, the hydrocarbon partial pressure of the flash stream in the present invention is set and controlled at between about 25 and about 175 kPa (about 4 and about 25 psia), such as between about 35 and about 100 kPa (about 5 and about 15 psia), for example between about 40 and about 75 kPa (about 6 and about 11 psia).

In one embodiment, the flash is conducted in at least one flash/separation vessel 5. Typically the flash is a one-stage process with or without reflux. The flash/separation vessel 5 is normally operated at about 275 to about 1400 kPa (about 40 to about 200 psia) pressure and its temperature is usually the same or slightly lower than the temperature of the flash stream 20 before entering the flash/separation vessel 5. Typically, the pressure at which the flash/separation vessel 5 operates is about 275 to about 1400 kPa (about 40 to about 200 psia), for example about 600 to about 1100 kPa (about 85 to about 155 psia), as a further example about 700 to about 1000 kPa (about 105 to about 145 psia), and in yet another example, the pressure of the flash/separation vessel 5 can be about 700 to about 760 kPa (about 105 to about 125 psia). The temperature at which the flash/separation vessel 5 operates, or the temperature of the inlet stream to the flash/separation vessel, is about 315 to about 560° C. (about 600 to about 1040° F.), such as about 370 to about 490° C. (about 700 to about 920° F.), for example about 400 to about 480° C. (about 750 to about 900° F.). Depending on the temperature of the mixture stream 12, generally about 50 to about 98% of the mixture stream being flashed is in the vapor phase, such as about 70 to about 95%.

The flash/separation vessel 5 is generally operated, in one aspect, to minimize the temperature of the liquid phase at the bottom of the vessel 5 because too much heat may cause coking of any non-volatiles present in the liquid phase.

The flash/separation vessel 5 is generally operated, in one aspect, to minimize the temperature of the liquid phase at the bottom of the vessel 5 because too much heat may cause coking of the non-volatiles in the liquid phase. Use of the secondary dilution steam stream 18 in the flash stream entering the flash/separation 5 vessel lowers the vaporization temperature because it reduces the partial pressure of the hydrocarbons (i.e., a larger mole fraction of the vapor is steam) and thus lowers the required liquid phase temperature. It may also be helpful to recycle a portion of the externally cooled flash/separation vessel 5 bottoms liquid 30 back to the flash/separator vessel to help cool the newly separated liquid phase at the bottom of the flash/separation vessel 5. Stream 27 can be conveyed from the bottom of the flash/separation vessel 5 to the cooler 28 via pump 37. The cooled stream 29 can then be split into a recycle stream 30 and export stream 22. The temperature of the recycled stream 30 would typically be about 260 to about 315° C. (about 500 to about 600° F.), for example about 270 to about 290° C. (about 520 to about 550° F.). The amount of recycled stream 30 can be about 80 to about 250% of the amount of the newly separated bottom liquid inside the flash/separation vessel 5, such as 90 to 225%, for example 100 to 200%.

The flash is generally also operated, in another aspect, to minimize the liquid retention/holding time in the flash/separation vessel 5. In one example embodiment, the liquid phase is discharged from the vessel 5 through a small diameter "boot" or cylinder 35 on the bottom of the flash/separation vessel 5. Typically, the liquid phase retention time in the flash/separation vessel 5 is less than 75 seconds, for example less than 60 seconds, such as less than 30 seconds, and often less than 15 seconds. The shorter the liquid phase retention/holding time in the flash/separation vessel 5, the less coking occurs in the bottom of the flash/separation vessel 5.

The vapor phase leaving the flash/separation vessel 5 may contain, for example, about 55 to about 70% hydrocarbons and about 30 to about 45% steam. The nominal boiling end point of the vapor phase is normally below about 760° C. (about 1400° F.), such as below about 675° C. (about 1250°

F.), for example below about 590° C. (about 1100° F.), as a further example below about 565° C. (about 1050° F.), and often below about 540° C. (about 1000° F.). The vapor phase is continuously removed from the flash/separation vessel 5 through an overhead pipe, which optionally conveys the vapor to an optional centrifugal separator 38 to remove trace amounts of entrained and/or condensed liquid. The vapor then typically flows into a manifold that distributes the flow to the lower convection section 23 or the radiant section 40 of the furnace 1.

The vapor phase stream 13 continuously removed from the flash/separation vessel 5 is preferably superheated in the pyrolysis furnace 1 lower convection section 23 to a temperature of, for example, about 425 to about 705° C. (about 800 to about 1300° F.) by the flue gas from the radiant section of the furnace. The vapor phase is then conveyed by the crossover piping 24 to the radiant section 40 of the pyrolysis furnace 1 to be cracked to produce an effluent comprising olefins, including ethylene and other desired light olefins, and byproducts.

The vapor phase stream 13 removed from the flash/separation vessel can optionally be mixed with a bypass steam stream 21 before being introduced into the furnace lower convection section 23.

Because the process of this invention results in significant removal (in the liquid phase 27 leaving the flash/separation vessel 5) of the coke- and tar-producing heavier hydrocarbon species, it may be possible to utilize a transfer line exchanger for quenching the effluent from the radiant section 40 of the pyrolysis furnace 1. Among other benefits, this will allow more cost-effective retrofitting of cracking facilities initially designed for lighter (uncontaminated) feeds, such as naphthas, or other liquid feedstocks with end boiling points generally below about 315° C. (about 600° F.), which have transfer line exchanger quench systems already in place. Co-pending Provisional Application Ser. No. 60/555,282, filed Mar. 22, 2004, the disclosure of which is fully incorporated herein, details a design for maximizing the benefits associated with use of a transfer line exchanger in conjunction with a process for cracking hydrocarbon feedstocks comprising non-volatile components.

The location and operating temperature of the flash/separation vessel 5 is selected to provide the maximum possible vapor feed which can be processed without excessive fouling/coking concerns. If the ratio of liquid is too high, valuable feed will be lost and the economics of the operation will be detrimentally affected. If the ratio of liquid is too low, deposition of salt and/or particulate matter in the convection tubes and the flash/separation vessel 5 may become a problem.

The percentage of given hydrocarbon feed discharged from the flash/separation vessel 5 as a vapor is a function of the hydrocarbon partial pressure in the flash/separation vessel 5 and of the temperature entering the vessel 5. The temperature of the hydrocarbon feedstock containing salt and/or particulate matter entering the flash/separation vessel 5 is highly dependent on the flue-gas temperature at that point in the convection section 3. This temperature will vary as the furnace load is changed, being higher when the furnace is at full load, and lower when the furnace 1 is at partial load. The flue-gas temperature in the convection section tube banks 2 and 6 are also functions of the extent of coking that has occurred in the furnace 1. When the furnace 1 is clean or lightly coked, heat transfer is improved and the flue-gas temperature at that point is correspondingly cooler than when the furnace 1 is heavily coked. The flue-gas temperature at any point is also a function of the combustion control exercised on the burners of the furnace 1.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A process for cracking an undesalted hydrocarbon feedstock containing salt and/or particulate matter, said process comprising:
    a. heating said undesalted hydrocarbon feedstock containing salt and/or particulate matter;
    b. feeding the undesalted hydrocarbon feedstock containing salt and/or particulate matter to a flash/separation vessel;
    c. separating the undesalted hydrocarbon feedstock containing salt and/or particulate matter into a vapor phase and a liquid phase, said liquid phase comprising a sufficient portion of the undesalted hydrocarbon feedstock to maintain salt and/or particulate matter in suspension;
    d. removing the vapor phase from the flash/separation vessel; and
    e. cracking the vapor phase to produce an effluent comprising olefins.

2. The process of claim 1 wherein steam is added at any step or steps prior to step (e).

3. The process of claim 1 wherein after separation of said undesalted hydrocarbon feedstock into a vapor phase and a liquid phase, at least 2% of said undesalted hydrocarbon feedstock is in the liquid phase.

4. The process of claim 1 wherein after separation of said undesalted hydrocarbon feedstock into a vapor phase and a liquid phase, at least 5% of said undesalted hydrocarbon feedstock is in the liquid phase.

5. The process of claim 2, wherein the steam comprises sour or treated process steam.

6. The process of claim 2, wherein the steam is superheated in the convection section of the pyrolysis furnace.

7. The process of claim 2, wherein steam is added between steps (a) and (b).

8. The process of claim 2, wherein steam is added between steps (a) and (b) and the temperature of the undesalted hydrocarbon feedstock containing salt and/or particulate matter is at a first temperature from about 150 to about 340° C. (about 300 to about 650° F.) before mixing with the steam, and the undesalted hydrocarbon feedstock containing salt and/or particulate matter is then further heated to a second temperature higher than the first temperature before step (b).

9. The process of claim 2, wherein steam is added to the vapor phase in the top portion of the flash/separation vessel.

10. The process of claim 2, wherein steam is added to the vapor phase downstream of the flash/separation vessel.

11. The process of claim 2, wherein said undesalted hydrocarbon feedstock containing salt and/or particulate matter is mixed with a fluid in addition to steam prior to step (d).

12. The process of claim 11 wherein said fluid mixed with said undesalted hydrocarbon feedstock containing salt and/or particulate, matter comprises a heavy hydrocarbon feedstock; said heavy hydrocarbon feedstock being sufficient to increase the T98 of the undesalted hydrocarbon feedstock containing salt and/or particulate matter by at least about 28° C. (about 50° F.) from the T98 of the undesalted hydrocarbon feedstock containing salt and/or particulate matter without said heavy hydrocarbon feedstock.

13. The process of claim 11 wherein said fluid mixed with said undesalted hydrocarbon feedstock containing salt and/or particulate matter comprises a heavy hydrocarbon feedstock; said heavy hydrocarbon feedstock being sufficient to increase the T95 of the undesalted hydrocarbon feedstock containing salt and/or particulate matter by at least about 14° C. (about 25° F.) from the T95 of the undesalted hydrocarbon feedstock containing salt and/or particulate matter without said heavy hydrocarbon feedstock.

14. The process of claim 12 wherein said heavy hydrocarbon feedstock, when mixed with said undesalted hydrocarbon feedstock containing salt and/or particulate matter, comprises between about 2 and about 75 wt. % of the mixture of the undesalted hydrocarbon feedstock containing salt and/or particulate matter and the heavy hydrocarbon feedstock.

15. The process of claim 12, wherein the heavy hydrocarbon feedstock comprises one or more of residues, crude oil, atmospheric pipestill bottoms, vacuum pipestill streams including bottoms, heavy non-virgin hydrocarbon streams from refineries, vacuum gas oils, atmospheric residue, low sulfur waxy residue, and heavy residue.

16. The process of claim 1, wherein the undesalted hydrocarbon feedstock containing salt and/or particulate matter is heated by indirect contact with flue gas in a first convection section tube bank of the pyrolysis furnace before mixing with steam.

17. The process of claim 16, wherein the undesalted hydrocarbon feedstock containing salt and/or particulate matter is heated by indirect contact with flue gas in a second convection section tube bank of the pyrolysis furnace before step (b).

18. The process of claim 1, wherein the temperature of the undesalted hydrocarbon feedstock containing salt and/or particulate matter in step (b) is from about 315 to about 560° C. (about 600 to about 1040° F.).

19. The process of claim 1, wherein the pressure in step (c) is from about 275 to about 1380 kPa (about 40 to about 200 psia).

20. The process of claim 1, wherein about 50 to about 95 percent of the undesalted hydrocarbon feedstock containing salt and/or particulate matter is in the vapor phase in step (d).

21. The process of claim 20, wherein about 60 to about 90 percent of the undesalted hydrocarbon feedstock containing salt and/or particulate matter is in the vapor phase in step (d).

22. The process of claim 1, further comprising conveying the vapor phase to a centrifugal separator to remove trace amounts of liquid before step (e).

23. The process of claim 1, wherein the vapor phase temperature entering the radiant section of the pyrolysis furnace is from about 425 to about 705° C. (about 800 to about 1300° F.).

24. The process of claim 1 further comprising quenching the effluent and recovering cracked product therefrom.

25. A process for cracking an undesalted hydrocarbon feedstock containing salt, said undesalted hydrocarbon feedstock containing salt further comprising non-volatile components and said process comprising:
   a. heating said undesalted hydrocarbon feedstock containing salt to a first temperature;
   b. adding steam to the undesalted hydrocarbon feedstock containing salt;
   c. further heating the undesalted hydrocarbon feedstock containing salt to a second temperature greater than the first temperature, said second temperature being such that a sufficient portion of the undesalted hydrocarbon feedstock containing salt remains in the liquid phase to maintain salt in suspension;
   d. feeding the undesalted hydrocarbon feedstock containing salt to a flash/separation vessel;
   e. separating the undesalted hydrocarbon feedstock containing salt into a vapor phase and a liquid phase, said liquid phase being rich in nonvolatile components and salt and said vapor phase being substantially depleted of non-volatile components and salt;
   f. removing the vapor phase from the flash/separation vessel;
   g. adding steam to the vapor phase; and
   h. cracking the vapor phase in a radiant section of a pyrolysis furnace to produce an effluent comprising olefins, said pyrolysis furnace comprising a radiant section and a convection section.

* * * * *